United States Patent
Kim et al.

(10) Patent No.: US 11,633,449 B2
(45) Date of Patent: Apr. 25, 2023

(54) METHOD FOR PREVENTING, ALLEVIATING, IMPROVING, OR TREATING THE FEMALE HORMONE CONTROLLING DISORDER SYNDROME OR SYMPTOMS COMPRISING A STEP OF ADMINISTERING GREEN TEA EXTRACT WHICH HAS MODIFIED AMOUNTS OF INGREDIENTS

(71) Applicant: AMOREPACIFIC CORPORATION, Seoul (KR)

(72) Inventors: Hyungsu Kim, Yongin-si (KR); Si Young Cho, Yongin-si (KR); A Young Kim, Yongin-si (KR); Wonseok Park, Yongin-si (KR); Yong Deog Hong, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 95 days.

(21) Appl. No.: 17/179,054

(22) Filed: Feb. 18, 2021

(65) Prior Publication Data

US 2021/0275621 A1 Sep. 9, 2021

(30) Foreign Application Priority Data

Mar. 9, 2020 (KR) .................. 10-2020-0028777

(51) Int. Cl.
| | | |
|---|---|---|
| *A61K 36/82* | (2006.01) | |
| *A61K 31/353* | (2006.01) | |
| *A61P 35/00* | (2006.01) | |
| *A61P 15/12* | (2006.01) | |
| *A23L 33/105* | (2016.01) | |
| *A23L 2/52* | (2006.01) | |
| *A23L 33/00* | (2016.01) | |

(52) U.S. Cl.
CPC .............. *A61K 36/82* (2013.01); *A23L 2/52* (2013.01); *A23L 33/105* (2016.08); *A23L 33/40* (2016.08); *A61K 31/353* (2013.01); *A61P 15/12* (2018.01); *A61P 35/00* (2018.01); *A23V 2002/00* (2013.01); *A61K 2236/331* (2013.01); *A61K 2236/333* (2013.01)

(58) Field of Classification Search
None
See application file for complete search history.

(56) References Cited

U.S. PATENT DOCUMENTS

| | | | |
|---|---|---|---|
| 9,211,298 B2 * | 12/2015 | Gao | ............... A23L 33/10 |
| 11,318,180 B2 * | 5/2022 | Chung | ............... A23L 33/105 |
| 2019/0091275 A1 | 3/2019 | Kim et al. | |
| 2019/0091276 A1 | 3/2019 | Kim et al. | |
| 2020/0397746 A1 * | 12/2020 | Jeong | ............... A61P 9/12 |

FOREIGN PATENT DOCUMENTS

| | | |
|---|---|---|
| EP | 1232756 A1 | 8/2002 |
| JP | 2006-129757 A | 5/2006 |
| JP | 4971535 B2 | 7/2012 |
| KR | 10-2001-0024462 A | 3/2001 |
| KR | 10-2006-0063797 A | 6/2006 |
| KR | 10-0596663 B1 | 7/2006 |
| KR | 10-0795566 B1 | 1/2008 |
| KR | 10-2019-0003247 A | 1/2019 |
| KR | 10-2019-0035473 A | 4/2019 |
| KR | 10-2019-0035474 A | 4/2019 |
| KR | 10-2019-0139472 A | 12/2019 |
| WO | 99/17612 A1 | 4/1999 |
| WO | 2004/110383 A2 | 12/2004 |
| WO | WO 2018/156960 * | 8/2018 |

OTHER PUBLICATIONS

Wu, A. et al. Effect of 2-Month Controlled Green Tea Intervention on Lipoprotein Cholesterol, Glucose, and Hormone Levels in Healthy Postmenopausal Women. Cancer Prevention Research 5(3)393-402, Mar. 2012. (Year: 2012).*

Kao, Y. et al. Modulation of Endocrine Systems and Food Intake by Green Tea Epigallocatechin Gallate. Endocrinology 141(3)980-987, 2000. (Year: 2000).*

Hara, Y. Tea Catechins and Their Applications as Supplements and Pharmaceutics. Pharmacological Research 64:100-104, 2011. (Year: 2011).*

Clement Y. Can Green Tea Do That? A Literature Review of the Clinical Evidence. Preventive Medicine 49(2-3)83-87, Aug./Sep. 2009. (Year: 2009).*

* cited by examiner

*Primary Examiner* — Ralph J Gitomer

(74) *Attorney, Agent, or Firm* — Merchant & Gould P.C.

(57) ABSTRACT

The present disclosure relates to a method for preventing, alleviating, improving or treating female hormone regulation disorder or symptoms, which contains a green tea extract with contents of ingredients changed. Specifically, the method according to an aspect of the present disclosure includes a step of administering an effective amount of a green tea extract, which contains (−)-gallocatechin gallate (GCG) and (−)-epigallocatechin gallate (EGCG) at specific contents, to a subject in need thereof, and may exhibit an effect of preventing, alleviating, improving or treating female hormone regulation disorder or symptoms.

10 Claims, 7 Drawing Sheets

METHOD FOR PREVENTING, ALLEVIATING, IMPROVING, OR TREATING THE FEMALE HORMONE CONTROLLING DISORDER SYNDROME OR SYMPTOMS COMPRISING A STEP OF ADMINISTERING GREEN TEA EXTRACT WHICH HAS MODIFIED AMOUNTS OF INGREDIENTS

CROSS-REFERENCE TO RELATED APPLICATION

This application claims, under 35 U.S.C. § 119, the priority of Korean Patent Application No. 10-2020-0028777, filed on Mar. 9, 2020, in the Korean Intellectual Property Office, the disclosure of which is incorporated herein by reference in its entirety.

BACKGROUND

1. Field

The present disclosure relates to a composition for preventing, alleviating, improving or treating female hormone regulation disorder or symptoms, which contains a green tea extract with contents of ingredients changed.

2. Description of the Related Art

Premenstrual syndrome (PMS) refers to physical and emotional symptoms occurring in women of childbearing ages. It is known that the premenstrual syndrome occurs before about one week before the start of each menstrual period, i.e., in the late luteal phase, as the level of progesterone in the body is decreased, which leads to decreased level of endorphin in the body. Although the intensity and duration of the premenstrual syndrome vary among individuals, it is known that 10-15% of women of childbearing ages suffer from severe physical and emotional stress, which can cause daily disability. In addition, severe menstrual cramps may cause severe abdominal pain together with nausea, vomiting, diarrhea, headache, dizziness, etc. as well as stress, depression, etc. caused by the pain. Since these can interfere with social activities at workplace, school, etc., its prevention, alleviation and treatment are very important for normal activities and lives of women.

The World Health Organization classifies premenstrual syndrome and menstrual cramps as diseases requiring treatment with code N94 (N943: premenstrual tension syndrome, N944: primary dysmenorrhea, N945: secondary dysmenorrhea). The number of patients receiving medical treatment due to menstrual cramps is increasing every year, and social medical expenses are also increasing. According to a survey by the National Health Insurance Service of Korea, it is reported that the number of patients treated for menstrual cramps (N94) was increased by 47.93% as of 2011 and the related health insurance expenditure was increased by 78.85% for 5 years (2007-2011). Accordingly, an effective and safe therapeutic agent for premenstrual syndrome and menstrual cramps is necessary in order to reduce social costs.

Therapeutic methods for alleviating and treating premenstrual syndrome and menstrual cramps include symptomatic therapy of keeping the abdomen warm, avoiding cold food, taking light exercise, taking a warm shower to help blood circulation, etc., a method of administering a prostaglandin inhibitor, estrogen therapy of maintaining anovulation by halting ovulation, progesterone therapy, testosterone therapy, medical treatment of administering a tocolytic, etc. Among them, the most frequently used method is medication of analgesics (typically, aspirin-based drugs) that suppresses prostaglandin synthesis. However, the use of aspirin-based drugs is limited to those who are allergic to aspirin or have troubles with digestive organs and, although the drugs are effective in reducing pain temporarily, they do not resolve the emotional anxiety or discomfort of premenstrual syndrome patients. In addition, too much dependence on or long-term medication of analgesics is undesirable because it may cause side effects such as digestive diseases, vascular diseases, etc. Accordingly, it is necessary to develop an agent for preventing, alleviating and treating premenstrual syndrome and menstrual cramps, which has superior efficacy and safety and can be medicated for a long period of time.

In general, women enter the climacteric around 50 years of age due to rapid decline in ovarian function. If the climacteric is continued, the secretion of the female hormone estrogen is decreased and, as a result, the risk of climacteric syndromes such as osteoporosis, hyperlipidemia, flushing, breast cancer and depression also increases. Therefore, researches on functional health foods and medications capable of effectively regulating biomarkers related with the blood estrogen level and diseases of climacteric women, which are important in the treatment and prevention of the climacteric syndromes, are being carried out actively.

According to surveys on climacteric women, estrogen is reported as a potent antiaging substance improving skin aging, which significantly improves skin elasticity, dryness, wrinkles, etc. when applied onto the skin. However, due to the limitation that such a hormone ingredient cannot be used in cosmetic products, the development of an active ingredient capable of replacing estrogen is necessary for improvement of skin aging in climacteric women.

Meanwhile, hormone replacement therapies that have been developed thus far can cause several side effects. For example, it is known that administration of estrogen as hormone replacement therapy has the risk of endometritis, breast cancer, gallbladder diseases, breast tenderness, mood changes, hypertension, thrombophlebitis, weight gain, etc. Therefore, it is not desirable to apply hormone replacement therapies for all climacteric women, and some climacteric women are reluctant to or drop out of hormone replacement therapies.

Accordingly, the development of a natural substance that can be used instead of hormones is necessary in order to alleviate the symptoms occurring in climacteric women.

SUMMARY

The present disclosure is directed to providing a natural plant-derived composition with excellent effect of preventing, alleviating, improving or treating female hormone regulation disorder or symptoms, which exhibits superior efficacy and safety and has no side effect.

In an exemplary embodiment, the present disclosure provides a composition for preventing, alleviating, improving or treating female hormone regulation disorder or symptoms, which contains a green tea extract containing 4-15 wt % of (−)-gallocatechin gallate (GCG) and 4-15 wt % of (−)-epigallocatechin gallate (EGCG) based on the total weight of the extract, as an active ingredient.

The extract and the composition according to an exemplary embodiment of the present disclosure have no side effect and are environment-friendly and safe because they are derived from a natural plant. In addition, they can exhibit superior effect of preventing, alleviating, improving or treating female hormone regulation disorder or symptoms.

DETAILED DESCRIPTION

Figure 1:
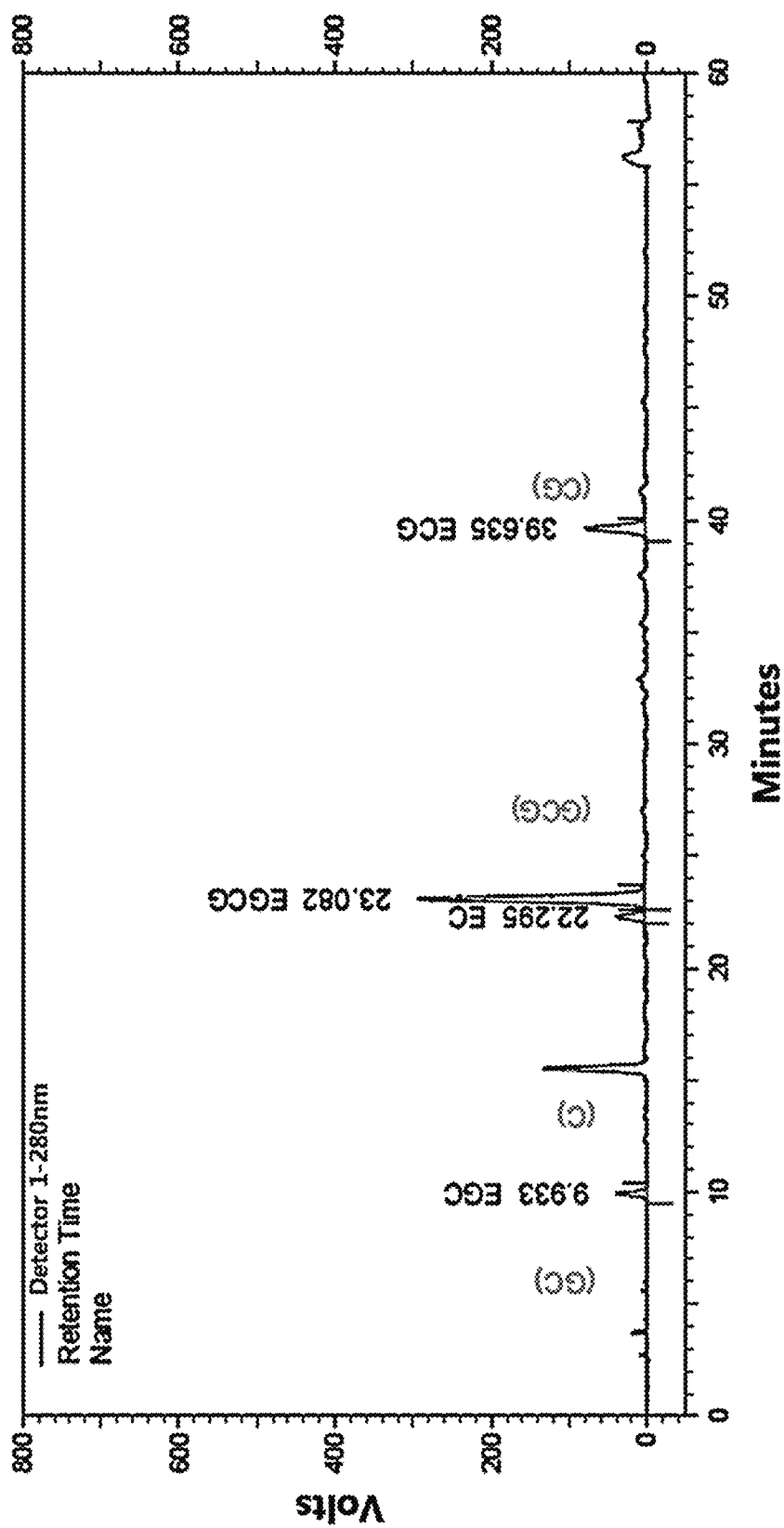
FIG. 1 shows the chromatogram of a notified green tea extract of Preparation Example 1 (sample 1).

Herein after, the present disclosure is described in detail.

In the present disclosure, "premenstrual syndrome (PMS)" refers to emotional, behavioral and physical symptoms occurring repetitively before menstruation. Specifically, the premenstrual syndrome may refer to physical symptoms such as abdominal distention, back pain, headache, breast pain, limb edema, etc., emotional symptoms such as mood changes, depression, anxiety, unpleasantness, aggressiveness, nervousness, confusion, chaos, etc., or psychological symptoms such as sleep disorder, appetite change, declined attention, lack of interest, social withdrawal, etc. These symptoms become gradually severe after ovulation, culminating around a week before the start of menstruation, and disappear within several days after menstruation.

In the present disclosure, "climacteric symptoms" may refer to physical and psychological symptoms such as weight gain, arthritis, muscle pain, hyperlipidemia, flushing, breast cancer, liver cell injury, joint pain, fatigue, excitement, headache, night sweats, insomnia, nervousness, anxiety, giddiness, declined attention, amnesia, depression, etc. or skin aging symptoms such as decreased skin elasticity, formation of skin wrinkles, decreased skin luster, skin dryness, etc.

In the present disclosure, a "green tea extract" includes an extract obtained from the evergreen shrub tea (Camellia sinensis), which belongs to the family Theaceae, or from the leaves of tea fermented by inoculating with Bacillus subtilis, regardless of extraction method, extraction solvent, extracted ingredients or extract type, as well as a fraction fractionated from the extract using a specific solvent. The tea may refer to one or more selected from a group consisting of the leaf, flower, stem, fruit, root and duramen of tea tree. Specifically, it may refer to leaf. In addition, the extract may be specifically in powder form. The extraction or fractionation may be performed using water, an organic solvent or a mixture solvent thereof. As the organic solvent, an alcohol such as isopropanol, acetone, hexane, ethyl acetate, carbon dioxide or a mixture solvent thereof may be used, although not being limited thereto. The extraction or fractionation may be performed at room temperature or elevated temperatures under a condition where the destruction of the active ingredients of green tea is prevented or minimized. The alcohol may be a $C_1$-$C_5$ lower alcohol. The number of method of the extraction or fractionation is not particularly limited. For example, such methods as cryoprecipitation extraction, ultrasonic extraction, reflux condensation extraction, hot water extraction, etc. may be used. Specifically, after extracting or fractionating active ingredients by cryoprecipitation or heating and, followed by filtration, the green tea extract of the present disclosure may be obtained by concentrating the filtrate under reduced pressure.

In the present disclosure "epicatechin" includes epigallocatechin (EGC), (−)-epicatechin (EC), (−)-epigallocatechin gallate (EGCG) and epicatechin 3-O-gallate (ECG).

In the present disclosure an "epicatechin epimer" includes gallocatechin (GC), catechin (C), (−)-gallocatechin gallate (GCG) and catechin gallate (CG).

In an aspect, the present disclosure may relate to a composition for preventing, alleviating, improving or treating female hormone regulation disorder or symptoms, which contains a green tea extract containing 4-15 wt % of (−)-gallocatechin gallate (GCG) and 4-15 wt % of (−)-epigallocatechin gallate (EGCG) based on the total weight of the extract as an active ingredient.

In another aspect, the present disclosure may relate to a method for preventing, alleviating, improving or treating female hormone regulation disorder or symptoms, which includes a step of administering an effective amount of a green tea extract containing 4-15 wt % of (−)-gallocatechin gallate (GCG) and 4-15 wt % of (−)-epigallocatechin gallate (EGCG) based on the total weight of the extract to a subject in need thereof.

In another aspect, the present disclosure may relate to a use of a green tea extract containing 4-15 wt % of (−)-gallocatechin gallate (GCG) and 4-15 wt % of (−)-epigallocatechin gallate (EGCG) based on the total weight of the extract for preparation of a composition for preventing, alleviating, improving or treating female hormone regulation disorder or symptoms.

In an exemplary embodiment, the female hormone regulation disorder or symptoms may be at least one selected from premenstrual syndrome, female climacteric symptom, estrogen deficiency and breast cancer.

In an exemplary embodiment, the GCG may be contained in an amount of 4 wt % or more, 5 wt % or more, 5.3 wt % or more, 5.59 wt % or more, 5.7 wt % or more, 6 wt % or more, 7 wt % or more, 8 wt % or more, 9 wt % or more, 10 wt % or more, 11 wt % or more, 12 wt % or more, 13 wt % or more or 14 wt % or more based on the total weight of the extract. In another exemplary embodiment, the GCG may be contained in an amount of 15 wt % or less, 14 wt % or less, 13 wt % or less, 12 wt % or less, 11 wt % or less, 10 wt % or less, 9 wt % or less, 8 wt % or less, 7 wt % or less, 6 wt % or less, 5.7 wt % or less, 5.59 wt % or less, 5.3 wt % or less or 5 wt % or less based on the total weight of the extract. When the GCG is contained within the above-described content ranges, a superior effect of preventing, alleviating, improving or treating female hormone regulation disorder or symptoms may be achieved.

In an exemplary embodiment, the EGCG may be contained in an amount of 4 wt % or more, 5 wt % or more, 5.2 wt % or more, 5.27 wt % or more, 5.5 wt % or more, 6 wt % or more, 7 wt % or more, 8 wt % or more, 9 wt % or more, 10 wt % or more, 11 wt % or more, 12 wt % or more, 13 wt % or more or 14 wt % or more based on the total weight of the extract. In another exemplary embodiment, the EGCG may be contained in an amount of 15 wt % or less, 14 wt % or less, 13 wt % or less, 12 wt % or less, 11 wt % or less, 10 wt % or less, 9 wt % or less, 8 wt % or less, 7 wt % or less, 6 wt % or less, 5.5 wt % or less, 5.27 wt % or less, 5.2 wt % or less or 5 wt % or less based on the total weight of the extract.

The green tea extract according to an aspect of the present disclosure, which contains EGCG at a significantly decreased content as compared to the existing green tea extract but contains GCG at a similar content to that of EGCG, may exhibit a superior effect of preventing, alleviating, improving or treating female hormone regulation disorder or symptoms.

In an exemplary embodiment, the total content of GCG and EGCG in the extract may be 30 wt % or less based on the total weight of the extract. In an aspect, the total content of GCG and EGCG may be 30 wt % or less, 25 wt % or less, 20 wt % or less, 18 wt % or less, 16 wt % or less, 15 wt % or less, 14 wt % or less, 12 wt % or less, 10.5 wt % or less, 10 wt % or less or 9 wt % or less based on the total weight of the extract. In another aspect, the total content of GCG and EGCG may be 8 wt % or more, 9 wt % or more, 10 wt % or more, 10.5 wt % or more, 12 wt % or more, 13 wt % or more, 14 wt % or more, 16 wt % or more, 18 wt % or more, 20 wt % or more or 25 wt % or more based on the total weight of the extract.

In an exemplary embodiment, the content of epicatechin in the extract may be 20 wt % or less based on the total weight of the extract. In an aspect, the epicatechin content may be 20 wt % or less, 18 wt % or less, 16 wt % or less, 15 wt % or less, 14 wt % or less, 12 wt % or less, 11 wt % or less or 10 wt % or less based on the total weight of the extract. In another aspect, the epicatechin content may be 9 wt % or more, 10 wt % or more, 11 wt % or more, 12 wt % or more, 13 wt % or more, 14 wt % or more, 16 wt % or more or 18 wt % or more based on the total weight of the extract.

In an exemplary embodiment, the total content of eight catechins EGCG, (−)-epigallocatechin (EGC), (−)-epicatechin (EC), epicatechin 3-O-gallate (ECG), GCG, gallocatechin (GC), catechin (C) and catechin gallate (CG) in the extract may be 19-30 wt % based on the total weight of the extract. In an aspect, the total content of the eight catechins may be 19 wt % or more, 21 wt % or more, 23 wt % or more, 24 wt % or more, 24.5 wt % or more, 25 wt % or more, 26 wt % or more, 27 wt % or more, 28 wt % or more or 29 wt % or more based on the total weight of the extract. In another aspect, the total content of the eight catechins may be 30 wt % or less, 29 wt % or less, 28 wt % or less, 27 wt % or less, 26 wt % or less, 25 wt % or less, 24.5 wt % or less, 24 wt % or less, 23 wt % or less or 21 wt % or less based on the total weight of the extract.

In an exemplary embodiment, a weight ratio of GCG:EGCG in the extract may be 1:0.5-2. In an aspect, the weight ratio of GCG:EGCG in the extract may be 1:0.5, 1:0.8, 1:1, 1:1.2, 1:1.5, 1:1.8 or 1:2.

When the weight ratio of GCG:EGCG is within the above-described ranges, a superior effect of preventing, alleviating, improving or treating female hormone regulation disorder or symptoms may be achieved safely without side effects.

In an exemplary embodiment, the extract may be an extract obtained by extracting one or more times with one or more of water and a $C_1$-$C_4$ alcohol. In an aspect, the alcohol may be ethanol. In another aspect, the alcohol may be 20% or higher, 30% or higher, 40% or higher, 50% or higher, 60% or higher or 70% or higher ethanol. In another aspect, the alcohol may be 70% or lower, 60% or lower, 50% or lower, 40% or lower or 30% or lower ethanol.

In an exemplary embodiment, the content of the green tea extract in the composition for alleviating or improving female hormone regulation disorder or symptoms may be 1-100 wt % based on the total weight of the composition. In an aspect, the content of the extract in the composition may be 1 wt % or more, 10 wt % or more, 20 wt % or more, 30 wt % or more, 40 wt % or more, 50 wt % or more, 60 wt % or more, 70 wt % or more, 80 wt % or more or 90 wt % or more. In another aspect, the content of the extract in the composition may be 100 wt % or less, 90 wt % or less, 80 wt % or less, 70 wt % or less, 60 wt % or less, 50 wt % or less, 40 wt % or less, 30 wt % or less or 20 wt % or less.

In an exemplary embodiment, an administration dosage of the active ingredient may be 5-1000 mg/kg/day. In an aspect, the administration dosage may be 5 mg/kg/day or more, 100 mg/kg/day or more, 200 mg/kg/day or more, 300 mg/kg/day or more, 400 mg/kg/day or more, 500 mg/kg/day or more, 600 mg/kg/day or more, 700 mg/kg/day or more, 800 mg/kg/day or more or 900 mg/kg/day or more. In another aspect, the administration dosage may be 1000 mg/kg/day or less, 900 mg/kg/day or less, 800 mg/kg/day or less, 700 mg/kg/day or less, 600 mg/kg/day or less, 500 mg/kg/day or less, 400 mg/kg/day or less, 300 mg/kg/day or less, 200 mg/kg/day or less, 100 mg/kg/day or less, 50 mg/kg/day or less or 10 mg/kg/day or less.

In another exemplary embodiment, the extract can increase the activity of estrogen receptor beta (ER-β). Through this, it can alleviate or improve female hormone regulation disorder or symptoms, e.g., premenstrual syndrome or climacteric symptoms.

In an exemplary embodiment, the composition for alleviating or improving female hormone regulation disorder or symptoms may be a comestible, pharmaceutical or cosmetic composition. More specifically, if the female hormone regulation disorder or symptom is a skin disease or symptom, e.g., a climacteric skin symptom, the composition for alleviating or improving female hormone regulation disorder or symptoms may be a cosmetic composition.

A formulation of the comestible composition is not particularly limited. For example, the composition may be formulated into a tablet, a granule, a pill, a powder, a liquid such as a drink, a caramel, a gel, a bar, a tea bag, etc. Each formulation of the comestible composition may be prepared without difficulty by those of ordinary skill in the art by mixing the active ingredient with an ingredient in consideration of the formulation or purpose of use. A synergistic effect may be achieved when an additional ingredient is used. The comestible may also be a functional health food.

The composition may be administered by various methods such as simple ingestion, drinking, injection, spraying, squeezing, etc.

For the comestible composition according to an aspect of the present disclosure, determination of the administration dosage of the active ingredient is within the level of those of ordinary skill in the art and may vary depending on various factors such as the age and health condition of a subject, the presence of a complication, etc.

For example, the comestible composition according to an aspect of the present disclosure may be various foods such as chewing gum, caramel, candy, ices, confectionery, etc., beverages such as soft drinks, mineral water, alcoholic beverages, etc., or functional health food products such as vitamins, minerals, etc.

In addition, the comestible composition according to an aspect of the present disclosure may contain various nutrients, vitamins, minerals (electrolytes), flavorants such as synthetic flavorants or natural flavorants, colorants, extenders (cheese, chocolate, etc.), pectic acid and its salts, alginic acid and its salts, organic acids, protective colloidal thickeners, pH control agents, stabilizers, antiseptics, glycerin, alcohols, carbonating agents used in carbonated drinks, etc. In addition, the comestible composition according to an aspect of the present disclosure may contain a pulp for preparing natural fruit juice, fruit juice drinks and vegetable drinks. These ingredients may be used independently or in combination. Although the proportion of the additives is of no great importance, they are usually contained in a range of about 0-60 parts by weight per 100 parts by weight of the composition according to an aspect of the present disclosure.

The pharmaceutical composition according to an aspect of the present disclosure may be administered orally or parenterally, e.g., rectally, topically, transdermally, intravenously, intramuscularly, intraperitoneally, subcutaneously, etc. A formulation for oral administration may be a tablet, a pill, a soft or hard capsule, a granule, a powder, a fine granule, a liquid, an emulsion or a pellet, although not being limited thereto. A formulation for parenteral administration may be a solution, a suspension, an emulsion, a gel, an injection, a medicinal drop, a suppository, a patch or a spray, although not being limited thereto. The formulation may be prepared easily according to common methods in the art and my further contain a surfactant, an excipient, a wetting agent, an emulsification accelerator, a suspending agent, a salt or buffer for control of osmotic pressure, a colorant, a flavor, a stabilizer, an antiseptic, a preservative or other commonly used adjuvants.

The composition according to an aspect of the present disclosure may also contain a pharmaceutically acceptable salt. The salt may include: (1) an acid addition salt formed from an inorganic acid such as hydrochloric acid, hydrobromic acid, sulfuric acid, nitric acid, phosphoric acid; or formed from an organic acid such as acetic acid, propionic acid, hexanoic acid, cyclopentylpropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, ethane-1,2-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid or muconic acid; or (2) a salt formed when an acidic proton present in the parent compound is replaced.

The application amount or administration dosage of the pharmaceutical composition according to an aspect of the present disclosure will vary depending on the age, sex and body weight of a subject, pathological condition and severity thereof, administration route or the discretion of a diagnoser. Determination of the administration dosage of the active ingredient based on these factors is within the level of those of ordinary skill in the art.

The cosmetic composition according to an aspect of the present disclosure may contain a cosmetically or dermatologically acceptable medium or base. It may be provided in the form of all topically applicable formulations, e.g., a solution, a gel, a solid, an anhydrous paste, an oil-in-water emulsion, a suspension, a microemulsion, a microcapsule, a fine granule, an ionic (liposomal) or nonionic vesicle, a cream, a lotion, a powder, an ointment, a spray or a conceal stick. These compositions may be prepared according to common methods in the art. In addition, the cosmetic composition may be in the form of an aerosol composition further containing a propellant compressed into a foam.

The formulation of the cosmetic composition is not particularly limited and may be selected appropriately depending on purposes. For example, the cosmetic composition may be formulated into a skin lotion, a skin softener, a skin toner, a lotion, a milk lotion, a moisturizing lotion, a nourishing lotion, a massage cream, a nourishing cream, a moisturizing cream, a hand cream, a foundation, an essence, a nourishing essence, a pack, a soap, a cleansing foam, a cleansing lotion, a cleansing cream, a cleansing water, a powder, a body lotion, a body cream, a body oil, a body cleanser, a body essence, etc.

When the formulation of the present disclosure is a paste, a cream or a gel, an animal fiber, a plant fiber, a wax, paraffin, starch, tragacanth, a cellulose derivative, polyethylene glycol, silicone, bentonite, silica, talc, zinc oxide, etc. may be used as a carrier ingredient.

When the formulation of the present disclosure is a powder or a spray, lactose, talc, silica, aluminum hydroxide, calcium silicate, polyamide powder, etc. may be used as a carrier ingredient. In particular, when the formulation is a spray, it may further contain a propellant such as chlorofluorohydrocarbon, propane/butane or dimethyl ether.

When the formulation of the present disclosure is a solution or an emulsion, a solvent, a solubilizer or an emulsifier may be used as a carrier ingredient. For example, water, ethanol, isopropanol, ethyl carbonate, ethyl acetate, benzyl alcohol, benzyl benzoate, polyethylene glycol, 1,3-butylene glycol, an aliphatic glycerol ester or a fatty acid ester of sorbitan may be used.

When the formulation of the present disclosure is a suspension, a liquid diluent such as water, ethanol or polyethylene glycol, a suspending agents such as ethoxylated isostearyl alcohol, polyoxyethylene sorbitol ester and polyoxyethylene sorbitan ester, microcrystalline cellulose, aluminum metahydroxide, bentonite, agar, tragacanth, etc. may be used as a carrier ingredient.

When the formulation of the present disclosure is a surfactant-containing cleanser, an aliphatic alcohol sulfate, an aliphatic alcohol ether sulfate, sulfosuccinic monoester, isethionate, an imidazolinium derivative, methyl taurate, sarcosinate, a fatty acid amide ether sulfate, an alkyl amidobetaine, an aliphatic alcohol, a fatty acid glyceride, a fatty acid diethanolamide, a vegetable oil, a lanolin derivative, an ethoxylated glycerol fatty acid ester, etc. may be used as a carrier ingredient.

The cosmetic composition may further contain, in addition to the green tea extract, a functional additive and an ingredient commonly contained in a cosmetic composition. The functional additive may include an ingredient selected from a group consisting of a water-soluble vitamin, an oil-soluble vitamin, a polypeptide, a polysaccharide, a sphingolipid and a seaweed extract.

The composition may further contain, in addition to the functional additive, an ingredient commonly contained in a cosmetic composition, if necessary. The additionally contained ingredient may be an oil, a fat, a humectant, an emollient, a surfactant, an organic or inorganic pigment, an organic powder, a UV absorbent, an antiseptic, a sterilizer, an antioxidant, a plant extract, a pH control agent, an alcohol, a colorant, a flavorant, a blood circulation promoter, a cooling agent, an antiperspirant, purified water, etc.

The present disclosure may provide the following exemplary embodiments.

A first exemplary embodiment may provide a method for preventing, alleviating, improving or treating female hormone regulation disorder or symptoms, which includes a step of administering an effective amount of a green tea extract comprising 4-15 wt % of (−)-gallocatechin gallate (GCG) and 4-15 wt % of (−)-epigallocatechin gallate (EGCG) based on the total weight of the extract to a subject in need thereof.

A second exemplary embodiment may provide the method according to the first exemplary embodiment, wherein the female hormone regulation disorder or symptom is at least one selected from premenstrual syndrome, climacteric symptom, estrogen deficiency and breast cancer.

A third exemplary embodiment may provide the method according to any of the first exemplary embodiment and the second exemplary embodiment, wherein a weight ratio of GCG:EGCG in the extract is 1:0.5-2.

A fourth exemplary embodiment may provide the method according to one or more of the first to third exemplary embodiments, wherein the extract is an extract obtained by extracting one or more times with one or more of water and a $C_1$-$C_4$ alcohol.

A fifth exemplary embodiment may provide the method according to one or more of the first to fourth exemplary embodiments, wherein the content of the extract in the composition is 1-100 wt % based on the total weight of the composition.

A sixth exemplary embodiment may provide the method according to one or more of the first to fifth exemplary embodiments, wherein an administration dosage of the active ingredient is 5-1000 mg/kg/day.

A seventh exemplary embodiment may provide the method according to one or more of the first to sixth exemplary embodiments, wherein the composition is a comestible, pharmaceutical or cosmetic composition.

Hereinafter, the present disclosure is described in more detail through preparation examples, examples and test examples. However, those preparation examples, examples and test examples are provided only for the understanding of the present disclosure and the scope of the present disclosure is not limited by the preparation examples, examples and test examples.

[Preparation Example 1] Preparation of Notified Green Tea Extract and High-Temperature-Processed Green Tea Extract After adding 1000 mL of 50% (v/v) ethanol to 100 g of green tea (*Camellia sinensis*, Jeju O'Sulloc Farm), the mixture was refluxed at 60° C. for 1 hour under stirring. After cooling to room temperature and filtering, 23 g of a notified green tea extract (GT-LE-35CAT, sample 1) was obtained as deep brown powder by distilling the obtained solution under reduced pressure (yield: 23%).

Meanwhile, for preparation of a high-temperature-processed green tea extract, 1000 mL of 50% (v/v) ethanol was added to 100 g of green tea (*Camellia sinensis*, Jeju O'Sulloc Farm) and the mixture was refluxed at 60° C. for 1 hour under stirring. After concentration, the resulting solution was stirred for 1-7 hours under steam flow at 1.5 kgf/cm². After cooling to room temperature and filtering insoluble materials, 10 g of a high-temperature-processed green tea extract was obtained by concentrating the solution under reduced pressure. For high-temperature-processed green tea extracts obtained at different stirring times (1-7 hours), the change in the content of eight catechins was measured using an apparatus described in Table 1. It was confirmed that the conversion of EGCG to GCG by heat was highest at 5 hours and the amount of the eight catechins did not decrease any more. 10 g of the obtained high-temperature-processed green tea extract (HTP-GTE) was designated as sample 2.

Figure 2:
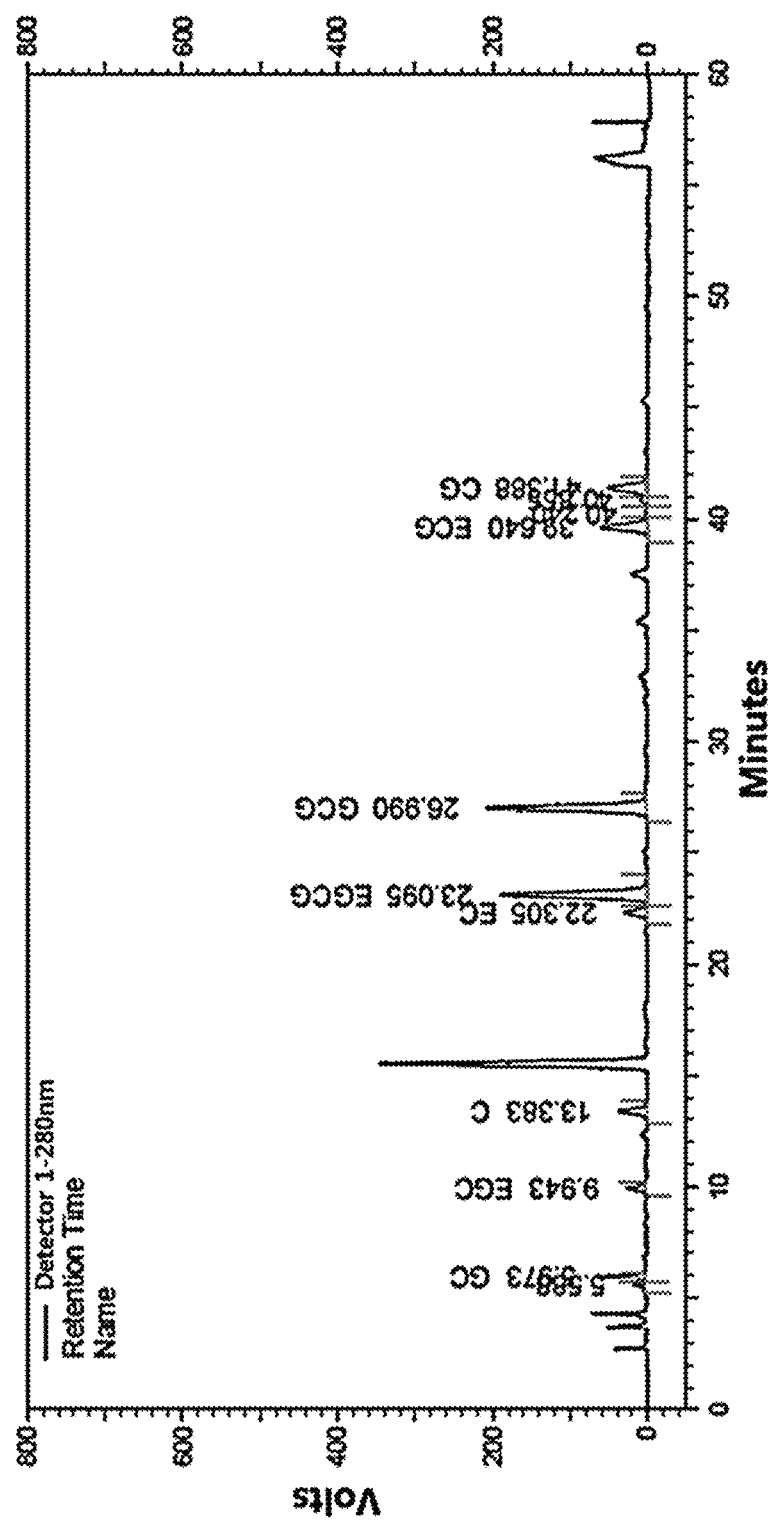
FIG. 2 shows the chromatogram of a high-temperature-processed green tea extract according to an aspect of the present disclosure (sample 2).

A result of analyzing the composition of the two obtained extracts and the analysis condition are shown in Table 1 (composition analysis condition for samples 1 and 2), Table 2 (composition analysis result for sample 1) and Table 3 (composition analysis result for sample 2). In addition, the chromatograms of the two extracts are shown in FIG. 1 (sample 1) and FIG. 2 (sample 2). It was confirmed that the sample 2 has a composition different from that of the existing green tea extract. Specifically, the sample 2 had significantly lower contents of EGCG (5.27 wt %), EGC (3.53 wt %) and total catechins (24.41 wt %) as compared to the sample 1, but also contained four epicatechin epimers not found in the sample 1.

TABLE 1

| Column | Thermo Fisher C18 5 μm, 4.6 × 250 mm |
|---|---|
| Detector | UV 280 nm |
| Dilution | Gradient |
| | A = 0.1% TFA (trifluoroacetic acid) in water |
| | B = acetonitrile |
| Gradient profile | 0 min A (90): B (10) |
| | 30 min A (85): B (15) |
| | 42 min A (80): B (20) |
| | 44 min A (5): B (95) |
| | 49 min A (90): B (10) |
| Flow rate | 1 mL/min |
| Injection volume | 20 μL |

TABLE 2

| | GC | EGC | Caffeine | C | EC | GCG | EGCG | CG | ECG | Total epicatechins | Total epicatechin epimers | Total catechins |
|---|---|---|---|---|---|---|---|---|---|---|---|---|
| Sample 1 | 0 | 9.16 | 3.21 | 0 | 3.63 | 0 | 20.93 | 0 | 2.62 | 36.34 | 0 | 36.34 |

TABLE 3

| | GC | EGC | Caffeine | C | EC | GCG | EGCG | CG | ECG | Total epicatechins | Total epicatechin epimers | Total catechins |
|---|---|---|---|---|---|---|---|---|---|---|---|---|
| Sample 2 | 4.9 | 3.53 | 3.9 | 1.57 | 0.95 | 5.59 | 5.27 | 1.3 | 1.3 | 11.05 | 13.36 | 24.41 |

(In Table 2 and Table 3, GC: gallocatechin, EGC: epigallocatechin, C: catechin, EC: (−)epicatechin, GCG: gallocatechin gallate, EGCG: epigallocatechin gallate, CG: catechin gallate, ECG: epicatechin 3-O-gallate)

(All the units in Table 2 and Table 3 are wt % of the corresponding ingredients based on the total weight of the green tea extract (samples 1 and 2))

[Preparation Example 2] Preparation of High-Temperature-Processed Green Tea Extracts with Different GCG:EGCG Ratios After further processing sample 2 of Preparation Example 1 by stirring under heating under steam of 1.5 kgf/cm² for 8 hours, the resulting solution was cooled to room temperature. After filtering insoluble materials and concentrating under reduced pressure, 10 g of sample 3 (GCG:EGCG=1:0.33) was obtained by further adding GCG (Table 4). In addition, after processing sample 2 of Preparation Example 1 by stirring under heating under steam of 1.5 kgf/cm² for 2 hours, the resulting solution was cooled to room temperature and 10 g of sample 4 (GCG:EGCG=1:3) was obtained by filtering insoluble materials and concentrating under reduced pressure (Table 5)

TABLE 4

|  | GC | EGC | Caffeine | C | EC | GCG | EGCG | CG | ECG | Total epicatechins | Total epicatechin epimers | Total catechins |
| --- | --- | --- | --- | --- | --- | --- | --- | --- | --- | --- | --- | --- |
| Sample 3 | 3.69 | 3.13 | 3.6 | 1.4 | 0.55 | 12.59 | 4.16 | 1.1 | 1.21 | 9.05 | 18.78 | 27.83 |

TABLE 5

|  | GC | EGC | Caffeine | C | EC | GCG | EGCG | CG | ECG | Total epicatechins | Total epicatechin epimers | Total catechins |
| --- | --- | --- | --- | --- | --- | --- | --- | --- | --- | --- | --- | --- |
| Sample 4 | 1.18 | 8.35 | 3.25 | 0.57 | 3.09 | 4.12 | 12.37 | 0.37 | 2.72 | 26.53 | 6.24 | 32.77 |

(In Table 4 and Table 5, GC: gallocatechin, EGC: epigallocatechin, C: catechin, EC: (−)epicatechin, GCG: gallocatechin gallate, EGCG: epigallocatechin gallate, CG: catechin gallate, ECG: epicatechin 3-O-gallate)

(All the units in Table 4 and Table 5 are wt % of the corresponding ingredients based on the total weight of the green tea extract (samples 3 and 4))

[Preparation Example 3] Preparation of Theanine

After extracting 10 kg of green tea leaf (*Camellia sinensis*, Jeju O'Sulloc Farm) with hot water and eluting the extract by treating with 1 N sodium hydroxide (NaOH) using a cation-exchange resin, the eluted solution was purified with activated carbon using 15% (v/v) ethanol (EtOH). After concentrating using a reverse osmosis (RO) membrane and purifying by column chromatography, 24.8 g of L-theanine was prepared through crystallization.

[Test Example 1] Evaluation of Premenstrual Syndrome-Improving Effect

For evaluation of the premenstrual syndrome-improving effect of the notified green tea extract, the high-temperature-processed green tea extract and theanine, 500-mg tablets containing 225 mg of sample 1 (notified green tea extract), 225 mg of sample 2 (high-temperature-processed green tea extract), 225 mg of sample 3, or 225 mg of sample 4 of Preparation Example 1 or 2, or 12.5 mg of theanine of Preparation Example 3, were prepared using a table-top single tableting machine (Erweka, Germany). In addition, a control drug was prepared in the same manner using 225 mg of maltodextrin (Daesang Corporation).

Figure 3:
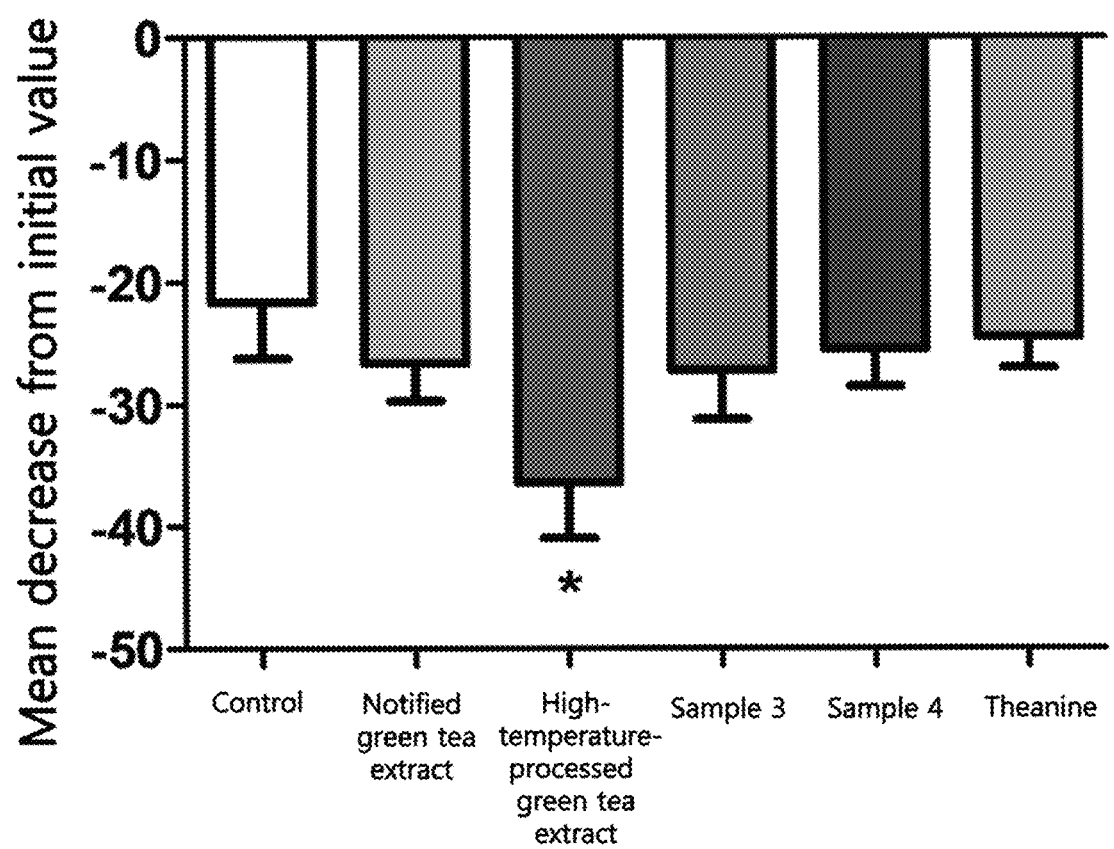
FIG. 3 shows a result of evaluating the effect of improving premenstrual syndrome based on the change in average total scores in self-written questionnaires in Test Example 1.

Those who have at least five symptoms including one or more physical symptom according to the diagnostic criteria described in Table 6 were selected as test subjects. From among 88 women of childbearing ages, in their 20s to 50s, 60 people were selected as test subjects. They were randomly divided into six groups of 10 people each: sample 1 (notified green tea extract) group, sample 2 (high-temperature-processed green tea extract) group, sample 3 group, sample 4 group, theanine group, control (control drug) group. The test subjects of each group were asked to answer premenstrual syndrome self-written questionnaires according to Table 7 before the start of menstruation and were asked to take the tablets for about 4 weeks until the end of the next menstruation, twice a day and two tablets per each time. That is to say, each group was given 900 mg of sample 1 (notified green tea extract), sample 2 (high-temperature-processed green tea extract), sample 3 or sample 4 or 50 mg of theanine every day. The subjects were asked to answer self-written questionnaires again before the start of the next menstruation and the change in average total scores and average mood scores was investigated. The result is shown in FIG. 3 (change in total scores) and FIG. 4 (change in mood scores).

TABLE 6

| Physical symptoms | Breast pain |
| --- | --- |
|  | Abdominal distention |
|  | Headache |
|  | Limb edema |
| Psychological symptoms | Depression |
|  | Anger |
|  | Nervousness |
|  | Anxiety |
|  | Confusion or chaos |
|  | Social withdrawal |

TABLE 7

Premenstrual syndrome self-written questionnaire

Please rate each item.

| Items | None (1 pt) | Slight (2 pts) | Moderate (3 pts) | Severe (4 pts) | Very severe (5 pts) |
|---|---|---|---|---|---|
| 1. Headache | | | | | |
| 2. Back pain | | | | | |
| 3. Sleep disorder | | | | | |
| 4. Memory decline | | | | | |
| 5. Poor judgement | | | | | |
| 6. Declined attention | | | | | |
| 7. Attention deficit | | | | | |
| 8. Declined work efficiency | | | | | |
| 9. Social withdrawal | | | | | |
| 10. Lack of interest in daily activities | | | | | |
| 11. Attracted by sweet and greasy food | | | | | |
| 12. Drink more coffee, tea, etc. | | | | | |
| 13. Abdominal distention or discomfort | | | | | |
| 14. Nausea | | | | | |
| 15. Feverish | | | | | |
| 16. Weight gain | | | | | |
| 17. Skin trouble | | | | | |
| 18. Breast pain | | | | | |
| 19. Swelling of hands and feet | | | | | |
| 20. Constipation | | | | | |
| 21. Bad mood | | | | | |
| 22. Solitude/loneliness | | | | | |
| 23. Sudden mood swings | | | | | |
| 24. Nervousness and anger | | | | | |
| 25. Depression | | | | | |
| 26. Anxiety | | | | | |

As seen from FIG. 3, the subjects who ingested sample 2 (high-temperature-processed green tea extract) according to an exemplary embodiment of the present disclosure showed significant decrease in average total scores as compared to the subjects who ingested the notified green tea extract, sample 3, sample 4 or theanine, which an amino acid abundant in green tea.

Figure 4:
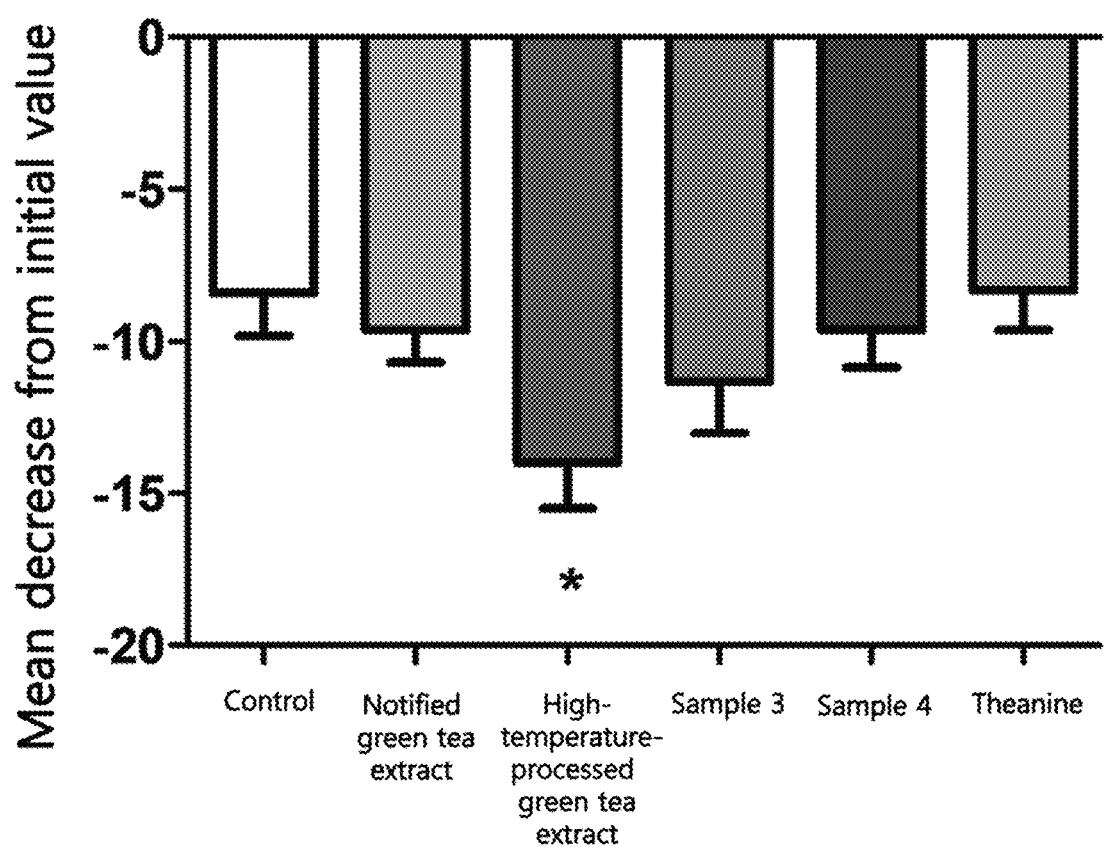
FIG. 4 shows a result of evaluating the effect of improving premenstrual syndrome based on the change in average mood scores in self-written questionnaires in Test Example 1.

In addition, as seen from FIG. 4, the subjects who ingested sample 2 (high-temperature-processed green tea extract) according to an exemplary embodiment of the present disclosure showed significant decrease in average scores for the psychological symptoms (items 21-26) described in the questionnaire of Table 7 as compared to the subjects who ingested the notified green tea extract, sample 3, sample 4 or theanine, which an amino acid abundant in green tea.

Based on these results, it was confirmed that sample 2 (high-temperature-processed green tea extract) according to an exemplary embodiment of the present disclosure is very effective in alleviating or improving the physical symptoms and psychological symptoms of premenstrual syndrome.

In particular, it was confirmed that, from among samples 2-4, which are high-temperature-processed green tea extracts, sample 2 wherein the GCG:EGCG weight ratio is about 1:0.9 showed significantly better effect of alleviating or improving the physical symptoms and psychological symptoms of premenstrual syndrome as compared to sample 3 and sample 4 wherein the GCG:EGCG weight ratio is about 1:0.3 and 1:3, respectively.

[Test Example 2] Evaluation of Climacteric Symptom-Improving Effect

For evaluation of the premenstrual syndrome-improving effect of the notified green tea extract, the high-temperature-processed green tea extract and theanine, 500-mg tablets containing 225 mg of sample 1 (notified green tea extract), 225 mg of sample 2 (high-temperature-processed green tea extract), 225 mg of sample 3, or 225 mg of sample 4 of Preparation Example 1 or 2, or 12.5 mg of theanine of Preparation Example 3, were prepared using a table-top single tableting machine (Erweka, Germany). In addition, a control drug was prepared in the same manner using 225 mg of maltodextrin (Daesang Corporation).

Figure 5:
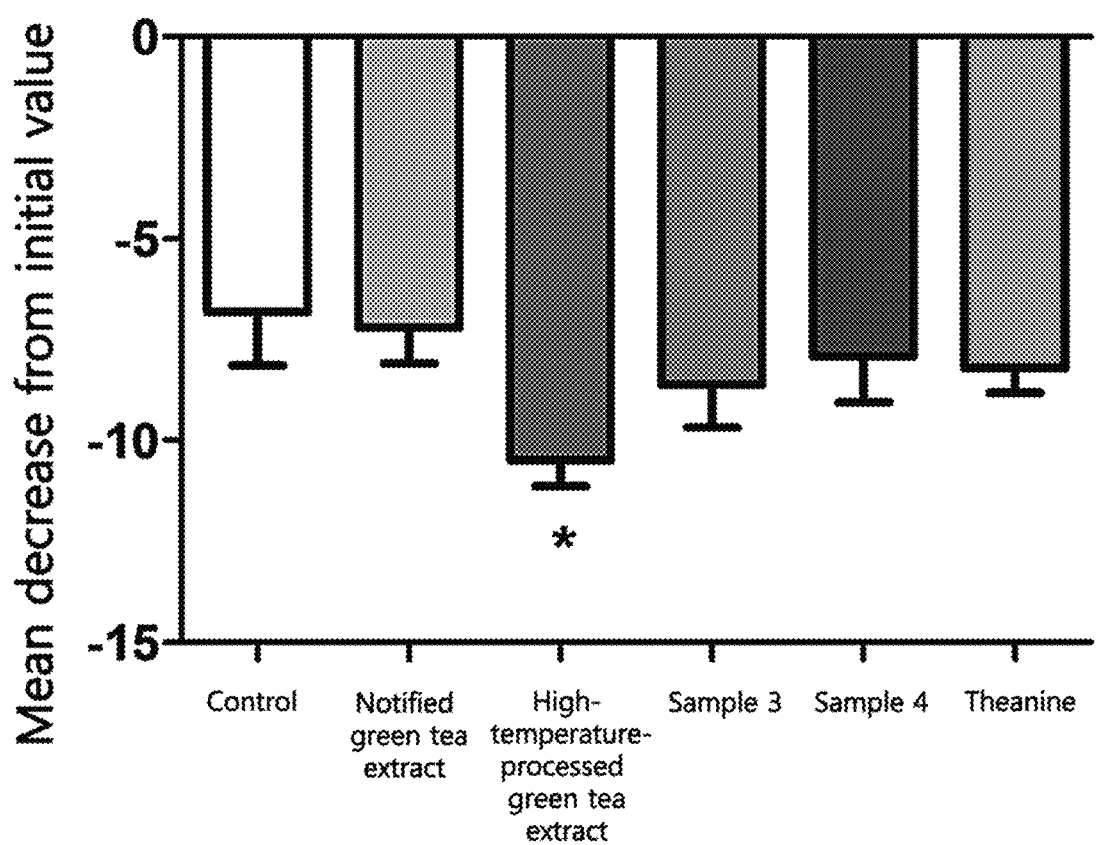
FIG. 5 shows a result of evaluating the effect of improving climacteric symptoms in Test Example 2.

60 women around the menopause (50 years old on average) whose total score for the menopause rating scale described in Table 8 was 5 or more points were randomly divided into 6 groups of 10 subjects each: sample 1 (notified green tea extract) group, sample 2 (high-temperature-processed green tea extract) group, sample 3 group, sample 4 group, theanine group and control (control drug) group. The 60 women of the sample groups were asked to answer according to the menopause rating scale described in Table 8 and then were given the tablets for 4 weeks, twice a day and two tablets per each time. That is to say, each group was given 900 mg of sample 1 (notified green tea extract), sample 2 (high-temperature-processed green tea extract), sample 3 or sample 4 or 50 mg of theanine every day. Then, they were asked to answer according to the symptom evaluation criteria again and the change in average total scores was investigated. The result is shown in FIG. 5.

TABLE 8

Menopause rating scale (MRS)

| | Never 0 pt | Occasionally (less than 5 times per month) 1 pt | Often(15 or more times per month) 2 pts | Frequently(2 or less times per week) 3 pts | Very frequently(4 or more times per week) 4 pts |
|---|---|---|---|---|---|
| 1. Hot flashes and sweating | | | | | |
| 2. Heart discomfort | | | | | |
| 3. Sleeping problems | | | | | |
| 4. Depressive mood | | | | | |
| 5. Irritability | | | | | |
| 6. Anxiety | | | | | |
| 7. Decline in memory and attention | | | | | |
| 8. Sexual problems | | | | | |
| 9. Bladder problems | | | | | |
| 10. Dryness of vagina | | | | | |
| 11. Joint and muscle discomfort | | | | | |

As seen from FIG. 5, the subjects who ingested sample 2 (high-temperature-processed green tea extract) according to an exemplary embodiment of the present disclosure showed significantly decreased average total scores as compared to the subjects who ingested the notified green tea extract, sample 3, sample 4 or theanine, which an amino acid abundant in green tea.

Through this, it was confirmed that sample 2 (high-temperature-processed green tea extract) according to an exemplary embodiment of the present disclosure is very effective in alleviating or improving the physical symptoms and psychological symptoms of climacteric symptom.

In addition, it was confirmed that, from among samples 2-4, which are high-temperature-processed green tea extracts, sample 2 wherein the GCG:EGCG weight ratio is about 1:0.9 showed significantly better effect of alleviating or improving the physical symptoms and psychological symptoms of climacteric syndrome as compared to sample 3 and sample 4 wherein the GCG:EGCG weight ratio is about 1:0.3 and 1:3, respectively.

[Test Example 3] Evaluation of Estrogen Receptor-Activating Effect

For evaluation of the effect of activating estrogen receptors alpha and beta (ERα/β) of the notified green tea extract, the high-temperature-processed green tea extract and theanine depending on the weight ratio of GCG:EGCG, a human ERα/β reporter assay panel (IB00421-48P, Indigo Bioscience) was treated with 20 μg/mL sample 1 (notified green tea extract), 20 μg/mL sample 2 (high-temperature-processed green tea extract), 20 μg/mL sample 3, or 20 μg/mL sample 4 of Preparation Example 1 or 2, or 1 μg/mL theanine of Preparation Example 3, for 24 hours and then the increased activity of the estrogen receptors ERα and ERβ was analyzed. As a control group, 100 pM 17b-estradiol included in the assay panel was used.

Specifically, ERα and ERβ are overexpressed and the ERE-luc reporter gene is included in the cells included in the human ERα/β reporter assay panel. If the activity of the estrogen receptors is increased upon treatment with the test substance, ERα and ERβ are bound to ERE and the expression of luciferase is induced. Therefore, the activity of ERα and ERβ can be determined by measuring light emission from the cells. The result is shown in FIG. 6.

Figure 6:
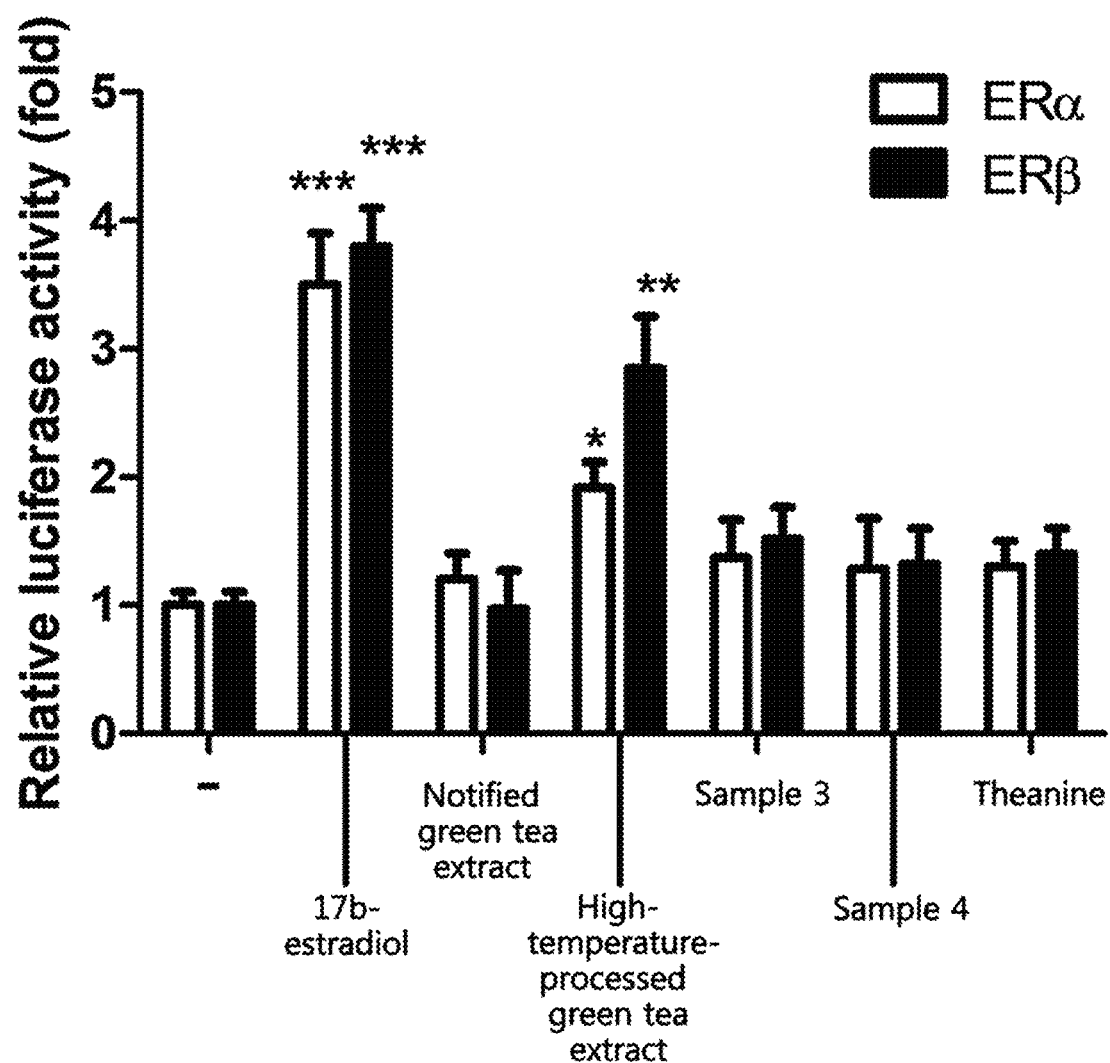
FIG. 6 shows a result of evaluating the effect of activating estrogen receptors in Test Example 3.

As seen from FIG. 6, when the degree of activation of the estrogen receptors ERα and ERβ was analyzed by measuring the activity of luciferase, whereas sample 1 (notified green tea extract), sample 3, sample 4 or theanine showed no receptor-activating effect, sample 2 (high-temperature-processed green tea extract) according to an exemplary embodiment of the present disclosure showed an effect of increasing the activity of the estrogen receptors ERα and ERI3. Through this, it can be seen that the high-temperature-processed green tea extract according to an exemplary embodiment of the present disclosure can exhibit the effect of alleviating or improving premenstrual syndrome or climacteric symptoms by increasing the activity of the estrogen receptors ERα and ERI3.

In particular, from among samples 2-4, which are high-temperature-processed green tea extracts, sample 2 wherein the GCG:EGCG weight ratio is about 1:0.9 showed significantly better effect of increasing the activity of the estrogen receptors ERα and ERβ as compared to sample 3 and sample 4 wherein the GCG:EGCG weight ratio is about 1:0.3 and 1:3, respectively. For sample 3 and sample 4, the effect was similar to that of the notified green tea extract or theanine.

In addition, as seen from FIG. 6, it was confirmed that, whereas the control group 17b-estradiol increased the activity of the estrogen receptors ERα and ERβ to similar levels, sample 2 (high-temperature-processed green tea extract) according to an exemplary embodiment of the present disclosure increased the activity of ERβ remarkably higher than that of ERα. Whereas the activation of ERα leads to increased incidence of breast cancer through increased growth and division of breast cancer cells, ERβ suppresses the growth of the cancer cells by inhibiting the activity of ERα. Therefore, it is expected that the risk of breast cancer, which is known as the representative side effect of estrogen therapy, can be significantly decreased if the increase in the activity of ERβ is higher than that of ERα. Therefore, it was investigated in Test Example 4 whether the high-temperature-processed green tea extract of the present disclosure shows the side effect of promoting breast cancer cell growth.

[Test Example 4] Evaluation of MCF-7 Breast Cancer Cell Growth-Inhibiting Effect After treating MCF-7 cells (breast cancer cells) acquired from Korean Cell Line Bank with 20 μg/mL of the notified green tea extract, the high-temperature-processed green tea extract, sample 3 or sample 4 of Preparation Example 1 or 2, 1 μg/mL of theanine of Preparation Example 3 or 100 pM of 17b-estradiol for 48 hours, the number of cells was counted using a cell counting device (Countess, Thermo Fisher Scientific). The result is shown in FIG. 7.

Figure 7:
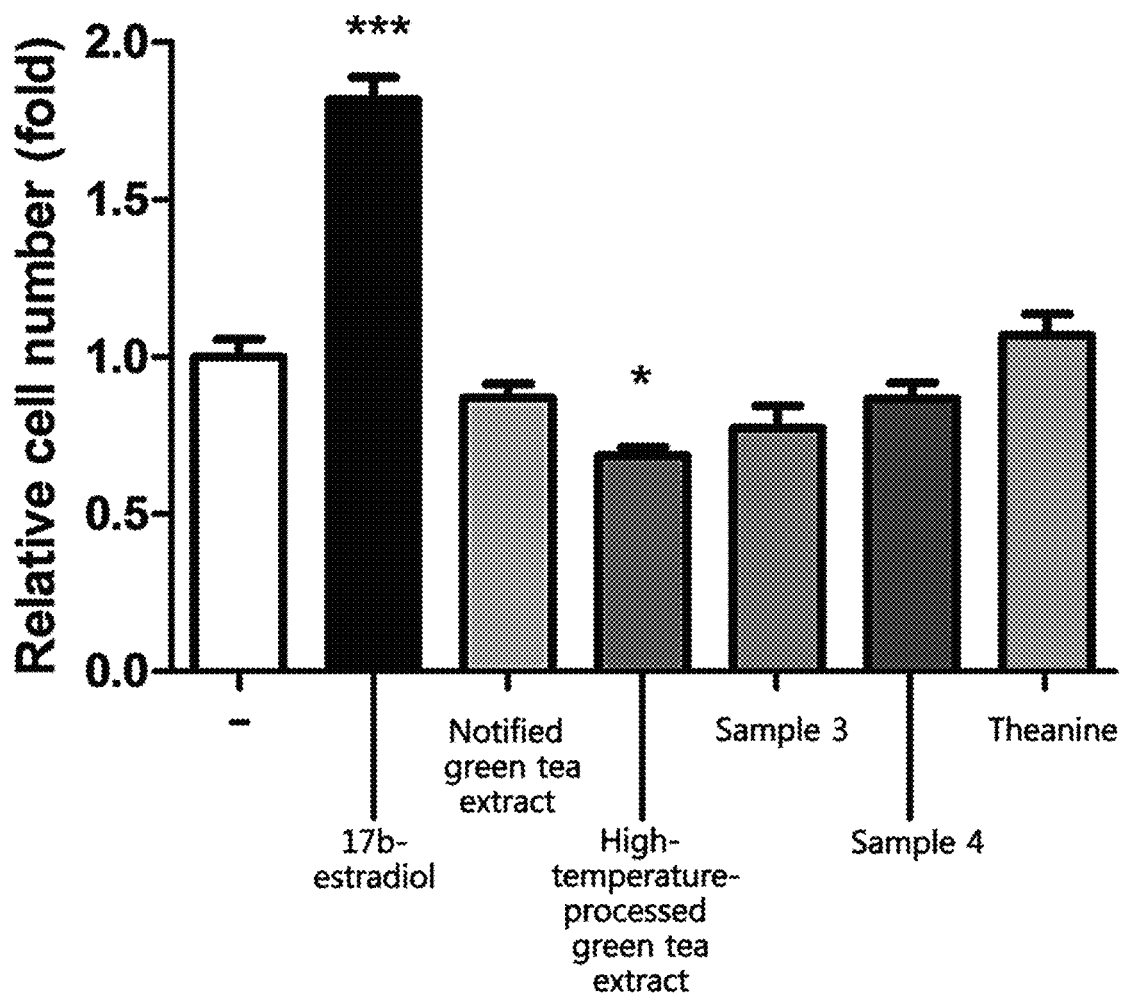
FIG. 7 shows a result of evaluating the effect of inhibiting the growth of MCF-7 breast cancer cells in Test Example 4.

As seen from FIG. 7, for the 17b-estradiol used as a positive control group for the evaluation of the estrogen receptor-activating effect in Test Example 3, the growth of the MCF-7 breast cancer cells was promoted significantly despite the remarkable effect of activating ERβ because the activity of ERα was also increased significantly to a similar level. In contrast, it was confirmed that sample 2 (high-temperature-processed green tea extract) according to an exemplary embodiment of the present disclosure does not show such side effect and, on the contrary, exhibits the effect of inhibiting the growth of the MCF-7 cells.

In addition, it was confirmed that sample 3 and sample 4, which are high-temperature-processed green tea extracts with GCG:EGCG weight ratios of about 1:0.3 and 1:3, respectively, had no significant effect on the activity of the estrogen receptors ERα and ERβ as in Test Example 3 and, thus, showed no significant effect on the growth of the MCF-7 cells.

Through this, it was confirmed sample 2 (high-temperature-processed green tea extract) according to an exemplary embodiment of the present disclosure exhibits excellent estrogen receptor-activating effect with no side effect of the existing estrogen therapy and, thus, can exhibit an effect of preventing or treating breast cancer.

[Formulation Example 1] Soft Capsule

A soft capsule filling solution was prepared by mixing 150 mg of sample 2 according to Example 1 with 440 mg of lactose, 430 mg of corn starch and 2 mg of magnesium stearate. Separately from this, a soft capsule sheet was prepared from 66 parts by weight of gelatin, 24 parts by weight of glycerin and 10 parts by weight of sorbitol. Then, a soft capsule was prepared by filling the sheet with the filling solution.

[Formulation Example 2] Tablet

After mixing 150 mg of sample 2 according to Example 1 with 15 mg of vitamin E, 15 mg of vitamin C, 250 mg of galactooligosaccharide, 60 mg of lactose and 140 mg of maltose and granulating the mixture using a fluidized-bed dryer, 8 mg of sugar ester was added. A tablet was prepared from the resulting composition according to a common method.

[Formulation Example 3] Drink

After mixing 80 mg of sample 2 according to Example 1 with 9 mg of vitamin E, 9 mg of vitamin C, 10 g of glucose, 0.6 g of citric acid and 25 g of oligosaccharide syrup, 400 mL of purified water was added. A drink was prepared by filling the mixture in a bottle and sterilizing at 30° C. for 4-5 seconds.

[Formulation Example 4] Granule

After mixing 150 mg of sample 2 according to Example 1 with 9 mg of vitamin E, 9 mg of vitamin C, 250 mg of anhydrous crystalline glucose and 550 mg of starch and forming the mixture into a granule using a fluidized-bed granulator, a granule was prepared by filling in a pouch.

[Formulation Example 5] Health Food

A health food was prepared by mixing 150 mg of sample 2 according to Example 1 with a vitamin mixture (70 μg of vitamin A acetate, 1.0 mg of vitamin E, 0.13 mg of vitamin $B_1$, 0.15 mg of vitamin $B_2$, 0.5 mg of vitamin $B_6$, 0.2 μg of vitamin $B_{12}$, 10 mg of vitamin C, 10 μg of biotin, 1.7 mg of nicotinamide and 50 μg of folic acid) and a mineral mixture (1.75 mg of ferrous sulfate, 0.82 mg of zinc oxide, 25.3 mg of magnesium carbonate, 15 mg of monopotassium phosphate, 55 mg of dicalcium phosphate, 90 mg of potassium citrate, 100 mg of calcium carbonate and 24.8 mg of magnesium chloride).

[Formulation Example 6] Health Drink 900 mL of a health drink was prepared by mixing 50 mg of sample 2 according to Example 1 with 1000 mg of citric acid, 100 g of oligosaccharide, 2 g of plum extract and 1 g of taurine and then adding purified water as balance.

While the specific exemplary embodiments of the present disclosure have been described in detail, it will be obvious to those having ordinary knowledge in the art that they are merely preferred exemplary embodiments and the scope of the present disclosure is not limited by them. Accordingly, the substantial scope of the present disclosure shall be defined by the appended claims and their equivalents.

What is claimed is:

1. A method for preventing, alleviating, improving or treating female hormone regulation disorder or symptoms, comprising a step of administering an effective amount of a green tea extract comprising 4-15 wt % of (−)-gallocatechin gallate (GCG) and 4-15 wt % of (−)-epigallocatechin gallate (EGCG) based on the total weight of the extract to a subject in need thereof, wherein a weight ratio of GCG:EGCG in the extract is 1:0.5-2.

2. The method according to claim 1, wherein the female hormone regulation disorder or symptom is at least one selected from premenstrual syndrome, climacteric symptom, estrogen deficiency and breast cancer.

3. The method according to claim 1, wherein the extract is an extract obtained by extracting one or more times with one or more of water and a $C_1$-$C_4$ alcohol.

4. The method according to claim 1, wherein the extract is formulated in the form of a composition, and a content of the extract in the composition is 1-100 wt % based on the total weight of the composition.

5. The method according to claim 1, wherein an administration dosage of the active ingredient is 5-1000 mg/kg/day.

6. The method according to claim 1, wherein the extract is formulated in the form of a composition, and the composition is a comestible, pharmaceutical or cosmetic composition.

7. The method according to claim 2, wherein the extract is formulated in the form of a composition, and the composition is a comestible, pharmaceutical or cosmetic composition.

8. The method according to claim 3, wherein the extract is formulated in the form of a composition, and the composition is a comestible, pharmaceutical or cosmetic composition.

9. The method according to claim 4, wherein the extract is formulated in the form of a composition, and the composition is a comestible, pharmaceutical or cosmetic composition.

10. The method according to claim 5, wherein the extract is formulated in the form of a composition, and the composition is a comestible, pharmaceutical or cosmetic composition.

* * * * *